United States Patent [19]

Leising et al.

[11] Patent Number: 5,156,774
[45] Date of Patent: Oct. 20, 1992

[54] THIOPHENE-RELATED COMPOUNDS ACTIVE IN NONLINEAR OPTICS, MATERIALS AND DEVICES CONTAINING THEM

[75] Inventors: Frederic Leising, Mornant; Remi Meyrueix; Gerard Mignani, both of Lyons, all of France

[73] Assignee: Flamel Technologies, Venissieux Cedex, France

[21] Appl. No.: 482,946

[22] Filed: Feb. 22, 1990

[30] Foreign Application Priority Data

Feb. 22, 1989 [FR] France .................. 89 02271

[51] Int. Cl.$^5$ .................. F21V 9/00; G02B 5/02; H01C 13/00
[52] U.S. Cl. .................. 252/582; 252/501.1; 252/518; 252/519
[58] Field of Search .................. 252/518, 519, 501.1, 252/582

[56] References Cited

U.S. PATENT DOCUMENTS 4,780,543 10/1988 Gordon et al. .

FOREIGN PATENT DOCUMENTS 0268354 5/1988 European Pat. Off. .

OTHER PUBLICATIONS

Chemical Abstracts, vol. 82, No. 11, Mar. 17, 1975, p. 413, 72683r.

*Primary Examiner*—Mark L. Bell
*Assistant Examiner*—Deborah Jones
*Attorney, Agent, or Firm*—Finnegan, Henderson, Farabow, Garrett & Dunner

[57] ABSTRACT

The present invention relates to new thiphene-related compounds of the general formula (I):

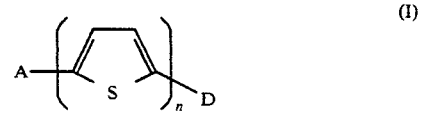

in which:

n is an integer between 1 and 10, advantageously between 1 and 4;

A is an electron-acceptor group; and D is an electron-donor group.

These compounds exhibit a high hyperpolarizability and an excellent photochemical stability and are employed especially in optical or electrooptical devices for their activity in nonlinear optics.

15 Claims, No Drawings

THIOPHENE-RELATED COMPOUNDS ACTIVE IN NONLINEAR OPTICS, MATERIALS AND DEVICES CONTAINING THEM

The invention relates to new thiophene-related compounds exhibiting high activity in nonlinear optics and, more particularly, to hyperpolarizable thiophene-related compounds capable, for example, of being added to a matrix to form a constituent of an electrooptical or optical device.

As pointed out by J. Zyss and I. Ledoux in their paper published in "L'Echo des Recherches", 1st quarter 1987, under the title "Molecules Organiques et Traitement du Signal Optique" ["Organic Molecules and Processing of the Optical Signal"], the development of optical telecommunications requires the construction of components employing materials of high nonlinear susceptibility of the second or of the third order.

Many compounds, both inorganic and organic, are employed in various forms such as solutions, polymers, doped polymers, monomolecular layers, liquid crystals, single crystals, liquid crystal polymers or the like.

The organic compounds are of great interest because the synthesis of a very large variety of products is generally possible. Moreover, most of the organic compounds exhibit a high resistance to external attack (moisture, acidity, oxidation and the like) and can be added to materials such as polymeric films or the like, permitting easy processing.

In their paper entitled "Design and Synthesis of Organic Molecular Compounds for Efficient Second Harmonic Generation," Publ. D. S. Chemla and J. Zyss, 1987, J. F. Nicoud and R. Y. Twieg list various molecules capable of being active in nonlinear optics. These molecules have a skeleton of carbon chains generally comprising aromatic rings substituted, on the one hand, by electron-donor groups and, on the other hand, by electron-acceptor groups. The delocalization of the electrons gives rise to high hyperpolarizability of the third and of the second order when the molecule is noncentrosymmetric.

Considerable research effort is continuously committed to discovering and manufacturing new compounds exhibiting an activity in nonlinear optics.

Thus, the invention proposes new thiophene-related compounds which exhibit high activity in nonlinear optics.

To this end, the invention proposes new thiophene-related compounds of following formula I:

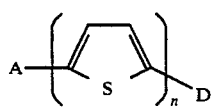

(I)

in which:

n is an integer from 1 and 10, advantageously from 1 to 4;

D denotes an electron-donor group having the following formula II:

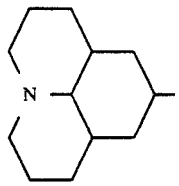

or is —$R_2(D_1)m$ in which $R_2$ is an aromatic hydrocarbon radical, preferably the phenylene radical, m is an integer from 1 to 3, and $D_1$ is a radical selected from the group consisting of amino, alkylamino, dialkylamino, arylamino, hydroxyl, thiol, alkylthio, arylthio, alkoxy, alkoxyphenyl, aryloxy, haloalkyl and oxy radicals, and especially

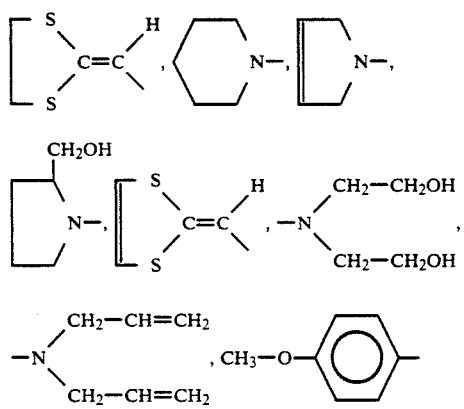

A denotes an electron-acceptor group selected from nitro and cyano radicals or of the general formula $$\begin{matrix} & & A_1 \\ & C=C & \\ H & & A_2 \end{matrix} \qquad (III)$$

in which $A_1$ and $A_2$ which are identical or different denote hydrogen, a cyano, nitro, phenyl sulfone or para-nitrophenyl radical or —$PO_3(R_5)_2$ in which $R_5$ is a lower alkyl radical such as the ethyl or propyl radical, with the proviso that $A_1$ and $A_2$ do not simultaneously denote hydrogen.

According to a preferred embodiment of the invention, the radicals D have the following formulae:

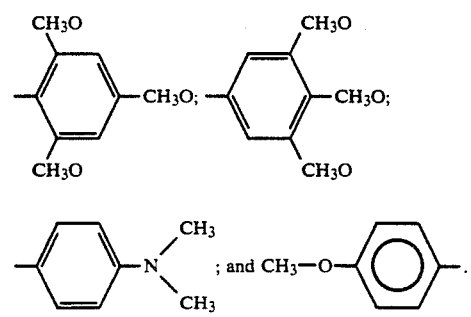

According to another embodiment of the invention, the preferred radicals $A_1$, $A_2$ of the invention are the cyano and nitro radicals, and advantageously the cyano/cyano, nitro/cyano, and cyano/nitro pairs.

The compounds of the invention are, for example, the compounds of the following formulae:

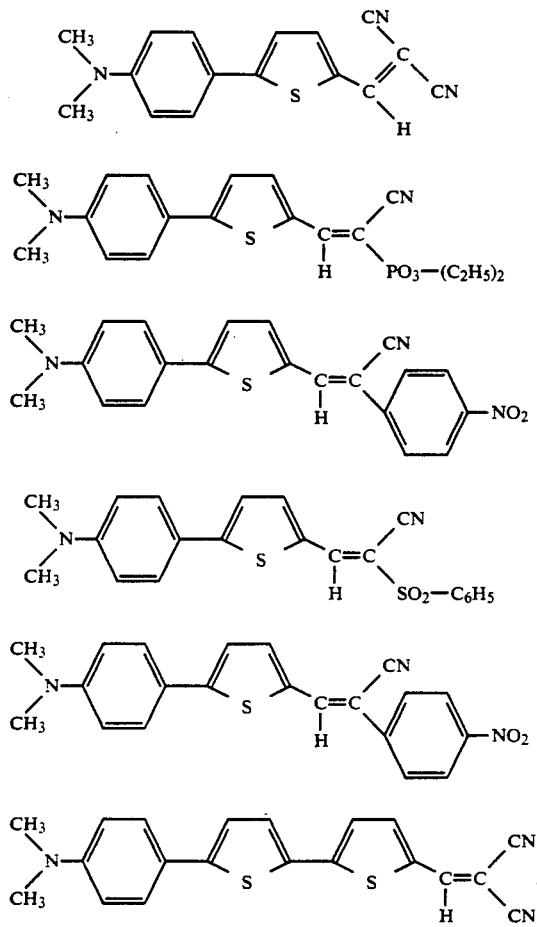

These compounds can be obtained by various processes of synthesis.

The invention also relates to compounds of high hyperpolarizability which are active in nonlinear optics, of following formula:

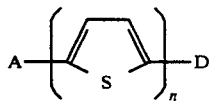

in which:
n is an integer between 1 and 10;
A is an electron-acceptor group; and
D is an electron-donor group.

According to a preferred embodiment of the invention, A and D have the meanings defined above.

The compounds of the invention of high hyperpolarizability are advantageously compounds of the trans form.

The compounds of the invention have the property of being active in nonlinear optics and are therefore capable of being employed in devices for electrooptical or purely optical processing, especially in the field of transducers, modulators, amplifiers and the like. In the application to frequency doubling, it is preferred that n be between 1 and 4, advantageously from 1 to 2. In fact, doubling of a harmonic requires transparency to the fundamental as in the 2nd harmonic and the $\lambda_{max}$ must be substantially lower than 450 nm in the case of a laser with pumping at 1060 nm. In contrast, in applications such as devices for electrooptical processing and parametric amplification, $\lambda_{max}$ can greatly exceed this value of 450 nm.

In fact, the activity of the materials in nonlinear optics is determined by the value of the coefficients and of hyperpolarizability of the second, third or nth order. The hyperpolarizability of a compound is directly related to the molecular dipole moment by the fundamental relationship:

$$\mu = \mu o = \beta . E = \gamma E . E = \gamma E . E . E = \ldots$$

in which:
$\mu$ and $\mu o$ denote the dipole moments in the presence and in the absence of an electromagnetic field, respectively;
E denotes the local electric or electromagnetic excitation field; and
$\alpha, \beta$ and $\gamma$ denote polarizability and hyperpolarizability coefficients.

In fact, the coefficient $\alpha$ is the coefficient of polarizability of the molecule and reflects its activity in linear optics. The coefficients $\beta$ and $\gamma$ denote the hyperpolarizability coefficients of the second and third order respectively. These coefficients reflect the anharmonicity of the electric potential in the molecule and are strongly dependent on the latter's symmetry and structure.

Furthermore, the odd-order coefficients, such as the coefficient $\gamma$, are never zero for any molecules. In contrast, the even-order coefficients, such as the coefficient $\beta$, are zero in the case of centrosymmetric molecules.

It is advantageous to employ molecules exhibiting a nonzero hyperpolarizability coefficient for applications in nonlinear optics such as, for example, electrooptical devices, electrooptical modulators, parametric amplifiers, frequency doubling devices or the like.

To evaluate and measure the coefficient $\beta$ of the molecules, the latter is determined by comparison with that of a reference molecule, namely urea. The measurement of the molecular hyperpolarizability $\beta$ of a compound can be generally carried out in an experiment for generating a second harmonic. It takes place in a solvent medium such as, for example, acetone, water or dimethyl sulfoxide. The method known by the name of the EFISH method is described in the papers by B. S. Levine et al., Appl. Phys. Lett., vol. 24, p. 445, 1974, and J. L. Houdar et al., J. Chem. Phys., vol. 67, p. 1926, 1977.

The product $\mu\beta(-\omega;\omega,o)$ can also be measured the electrooptical susceptibility $\chi^{(2)}(-\omega;\omega,o)$ of a doped and polarized PMMA film containing N active molecules per volume unit. The measurement of $\omega^{(2)}(-\omega;\omega,o)$ can be carried out by interferometry, as described in the paper by K. D. Singer et al., J. Opt. Soc. Am. B, vol. 4, No. 6, p. 968 et seq. (1987).

The relationship between $\mu\beta$ and $\omega^{(2)}$ is well known; it can be found, for example, in the paper by K. D. Singer et al., Appl. Phys. Lett., vol. 49, No. 5, p. 248 et seq. (1986).

The hyperpolarizability of the molecule can also be expressed by a static coefficient $\beta\mu$ which corresponds to the activity of the molecule at zero frequency and hence gives a measure of the intrinsic activity of the molecule. To do this, a measurement of $\beta\mu$ is carried out at a given frequency, using a Mach-Zender interferometer, and this value is then normalized to a zero hypothetical frequency by means of model calculations known as "two level model."

The method of measuring and calculating the static $\beta\mu$ is described in the paper, infra, by K. D. Singer et al. which appeared in J. Opt. Soc. Am. B, vol. 4, No. 6, pp. 968 et seq. (1987).

It is advantageous, furthermore, that the compounds which are active in nonlinear optics have a good photostability. In fact, as described in the paper, infra, by K. D. Singer et al., J. Opt. Soc. Am. B, vol. 4, No. 6, pp. 968 et seq. (1987), the hyperpolarizability $\beta(-\omega;\omega,0)$ is a function of the frequency $\omega$ of the light employed: $\beta$ will be proportionally higher the closer the frequency $\omega$ or the length $\lambda$ of the radiation will be to the absorption frequency $\omega_{max}$ or maximum wavelength of absorption $\omega_{max}$ of the molecule. However, at such a wavelength or frequency, most of the highly conjugated molecules turn out to be relatively unstable under laser radiation.

In contrast, the compounds of the invention exhibit a remarkable photochemical stability even under a radiation of wavelength close to the maximum wavelength of absorption $\omega_{max}$ of the molecule.

Another object of the present invention is to provide a process for the manufacture of compounds according to the present invention.

These compounds are, in fact, easily obtained in an original manner by means of a process comprising the following stages:

a) formation of an organozinc derivative of thiophene, preferably by successive action of butyllithium and of a zinc halide;

b) reaction of the organozinc derivative with a reactant D-X where D is as defined above and X is a leaving group such as, for example, tosyl or a halide such as a chloride or bromide or a compound of the type RY wherein R is aryl, e.g. phenyl, or alkyl, e.g. lower alkyl, and Y is a halogen, e.g. chlorine or bromine;

c) anionization of the product obtained on the second reactive position of thiophene, preferably by the action of butyllithium;

d) reaction of the carbanion obtained in stage c) with dimethylformamide (DMF); and e) reaction of the aldehyde obtained with an activated methylene group capable of reacting with the aldehyde to form a double bond, the activated methylene group being of the formula $(A_1)$—CH wherein $A_1$ and $A_2$ are as defined above.

Stage a) and stage b) can be carried out by employing the general methods described in Tetrahedron Letters, volume 28, number 43, page 5213 to 5216, 1987. Stages c) and d) are the transposition of the formation of an aldehyde according to the method described in Synthesis, 228 (1984); in J. Org. Chem. 40, 231 (1975; and in Synthesis 625 (1980).

The "polythiophenes" react like "thiophene."

The invention will be illustrated more clearly in the light of the examples given below solely by way of illustration and guidance.

EXAMPLE 1

Preparation of the compound of formula (i)

The process of manufacture described in this example can be used for the synthesis of the compounds of formula (ii) to (v) merely by changing the starting materials and operating conditions.

a) Preparation of:

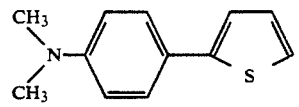

0.7 mole of dry thiophene in 250 ml of dry tetrahydrofuran (THF) was introduced into a round bottom flask and 0.64 mole of n-butyllithium (1.6 M in hexane) was then introduced after the solution had been cooled to $-20°$ C. 0.7 mole of $ZnCl_2$ was dissolved in 500 ml of dry THF and the two solutions were mixed. The whole was kept stirred for approximately 2 hours at ambient temperature. The solution obtained was introduced into the mixture: 0.00132 mole of palladium dibenzyl ketone $(Pd(DBA)_2)$, 0.00559 mole of triphenylphosphine (TPP) and 0.421 mole of parabromodimethylaniline. The whole was heated to reflux for 16 hours and then cooled before addition of water. An extraction was carried out with ethyl acetate. The product was recovered and dried over $MgSO_4$ and was then recrystallized from methanol. The solid recovered (44.64 g) had a melting point of 122° C.

b) Preparation of:

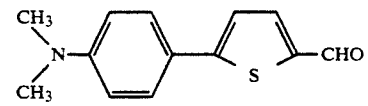

0.017 mole of the product obtained in a) was dissolved in 200 ml of dry THF. 10.6 $cm^3$ of a solution of n-BuLi at a concentration of 1.6 M in hexane were added to this solution, which was cooled to 0° C. The reaction continued for about 1 hour, and 2 ml of dimethylformamide were added; the reaction was then allowed to proceed for 16 hours at 25° C. After the mixture had been acidified, an extraction was carried out with ethyl acetate. After washing the organic phases with water and drying over $MgSO_4$, the solvent was evaporated off to recover a yellow solid with a melting point equal to 196° C. Infrared, ultraviolet or NMR spectrometry analyses and mass spectrography confirmed the structure shown above.

c) Preparation of the compound of formula (i)

$9.28 \times 10^{-3}$ mole of dicyanomethane, 4 drops of piperidine and $5.54 \times 10^{-3}$ mole of the compound prepared in b) were introduced into 120 ml of ethanol. After heating under reflux for 3 hours, the red precipitate formed was recovered by filtration and washing with hexane. The recovered product had a melting point of 217° C. Its structure was confirmed by spectrographic analyses. It had a maximum wavelength of absorption max in $CHCl_3$ medium equal to 510 nm for an extinction coefficient equal to 40700.

EXAMPLES 2 to 5

The compounds (ii) to (v) were prepared in a manner similar to the compound (i); however, the compounds reacted with the compound

[Structure: 4-(dimethylamino)phenyl-thiophene-CHO]

were, respectively:

CH₂—(CN)PO₃(OEt)₂, NC—CH₂—C₆H₄—NO₂,

C₆H₅—SO₂—CH₂—CN, and

O₂N—C₆H₄—CH₂—COOH.

The structures of the products obtained were verified by spectral and elemental analyses.

The characteristics of the products obtained are the following:

Ex. 2 prod. (ii) mp: 156° C. $\lambda_{max}$ (CHCl₃) =464 nm
$\epsilon$=25,900

Ex. 3 prod. (iii) mp: 298° C. $\lambda_{max}$ (CHCl₃) =488 nm
$\epsilon$=37,500

Ex. 4 prod. (iv) mp: 211° C. $\lambda_{max}$ (CHCl₃) =498 nm
$\epsilon$=36,400

Ex. 5 prod. (v) mp: 240° C. $\lambda_{max}$ (CHCl₃) =457 nm
$\epsilon$=28,200

EXAMPLE 6

In a manner similar to that in the preceding examples, the compound of the formula (0.020 mole)

[Structure: (CH₃)₂N-C₆H₄-thiophene-thiophene-CHO]

dissolved in 250 ml of ethanol was reacted with 0.022 mole of NC—CH₂—CN, in the presence of a catalytic quantity of piperidine. After heating under reflux for 5 hours, the brown-red precipitate formed was recovered by filtration, washing with hexane and drying. Its structure was verified by spectral analyses. It had a melting point equal to 215° C. and a max (CHCl₃) equal to 540 nm.

EXAMPLE 7

Synthesis of the compound of the formula

[Structure: CH₃O-C₆H₄-thiophene-CH=C(CN)₂ type]

The synthesis comprised the following 3 reaction stages:

a) [thiophene] + Br-C₆H₄-OCH₃ ⟶ (2)

[Structure: thiophene-C₆H₄-OCH₃]

Intermediate compound 1 b) CH₃—O—C₆H₄-thiophene-CHO

Intermediate compound 2 c) CH₃—O—C₆H₄-thiophene-CH=C(CN)₂

Compound VII (a) Synthesis of 2-paramethoxyphenylthiophene

[Structure: thiophene-C₆H₄-OCH₃] (1)

23.30 g of thiophene (0.277 mole) and 140 ml of dry THF were introduced into a 500 ml three-necked round bottom flask placed under nitrogen; after cooling to −20° C., 160 ml of butyllithium (46 M/1 in hexane) were run in slowly; the temperature was allowed to return to 0° C.; time 2 hours 30 min. 34.6 g (0.254 M) of ZnCl₂ and 275 ml of dry THF were charged under nitrogen into a one-liter three-necked vessel with mechanical stirring. After allowing to dissolve, the above solution was run in over 30 min; the reaction was slightly exothermic. 20 ml of THF were added again for rinsing. 0.3907 g (6.80 ×10⁻⁴ mole) of Pd(DBA)₂, 0.714 g (2.72 ×10³ mole) of TPP and 220 ml of dry THF were charged into a 2 liter three-necked vessel placed under nitrogen; after allowing to react (10 min), 45.9 g (0.245 mole) of para-bromoanisole were added and the above solution was run in at normal temperature; heating under reflux was carried out for 16 hours. After allowing to cool, water was added and the mixture was extracted with ethyl acetate; the material was washed with water, dried over MgSO₄ and was evaporated down; a solid was recovered. 27.3 g of a solid were obtained by recrystallization (melting point: 111° C.) (2-paramethoxyphenylthiophene).

Isolated yield: 58.6%.

(b) Synthesis of (2)

[Structure: CH₃—O—C₆H₄-thiophene-CHO] (2)

20.4 g (0.1073 mole) of 2-paramethoxyphenylthiophene obtained in the preceding stage and 170 ml of dry THF were introduced under nitrogen into a 500 ml three-necked vessel; this was cooled to −5, −10° C. and a butyllithium/hexane solution (1.6 M), 0.0972 mole of n-butyllithium was run in over 30 min. The mixture was left for 3 hours at 0° C. 9.7 g (0.133 M) of dry dimethylformamide (DMF) were then introduced. Reaction was allowed to proceed at ambient temperature for 16 hours. The material was hydrolyzed and extracted with ethyl acetate; it was dried over MgSO4 and 368 g or an orange-colored solid were recovered. Hot hexane was added and 16.8 g of a pale pink solid were recovered by filtration (melting point: 120–122.5° C.)

Isolated yield: 79.3%

(c) Synthesis of (VII)

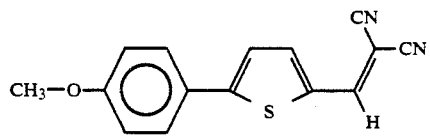 (7)

0.9 g (0.05 mole) of (2):

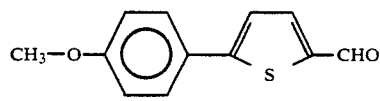

and 580 ml of absolute ethanol were introduced under nitrogen into a 1 liter three-necked vessel. The mixture was heated to 50° C. to dissolve (2); 5.9 g (0.0893 mole) of CN—CH2—CN and 10 drops of piperidine were then added. The material was heated under reflux for 5 min; an orange-colored precipitate was formed; refluxing was continued for 3 hours. The material was filtered; it was left with hexane and was dried for 16 hours in a desiccator. 11.9 g of an orange-colored solid were recovered (melting point: 195° C.).

Isolated yield (7): 89.5%

Analyses by infrared, ultraviolet and proton nuclear magnetic resonance confirmed the structure of the products.

$\lambda_{max}$ (CHCl3): 430 nm
($\epsilon$: 36,900)

EXAMPLE NO. 8

Synthesis of

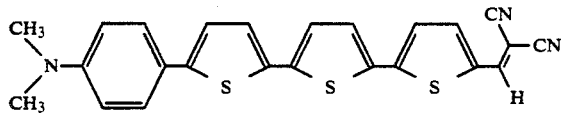

In a manner similar to the preceding examples, the compound of the formula (6.83 ×10⁻⁴ mole)

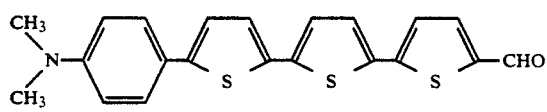

dissolved in 150 ml of ethanol was reacted with 0.15 g (2.27 ×10⁻³ mole) of NC—CH2—CN, in the presence of a catalytic quantity of piperidine. After heating to reflux for 1 hour, the dark red precipitate formed was recovered by filtration, washed with petane and dried under vacuum. Its structure was verified by spectral analyses. It exhibited the $\lambda_{max}$ (CHCl3) equal to 500 nm ($\epsilon$=22,700).

Melting point: 220° C.

ONL activity: $\beta(\omega, \omega, o)$. 7,470 ×10⁻⁴⁸ e.s.u.

The results of determinations of the hyperpolarizability coefficient and of the static coefficient $\beta\mu$ of certain of these products according to the methods described above are collated in the table below.

| Ex. | Compound | Hyperpolarizability coefficient $\beta$ $(-\omega,\omega,o)$ at $\lambda$ = 633 nm | Static coefficient $\beta\mu$ × 10⁻⁴⁸ e.s.u. | $\lambda$ max |
| --- | --- | --- | --- | --- |
| 1 | (i) | 7630 × 10⁻⁴⁸ e.s.u. | 1,200 | 510 nm + |
| 3 | (iii) | 1980 × 10⁻⁴⁸ e.s.u. | 510 | 490 nm |
| 6 | (vi) | 11500 × 10⁻⁴⁸ e.s.u. | 1,125 | 540 nm + |
| 7 | (vii) | 2500 × 10⁻⁴⁸ e.s.u. | 850 | 450 nm |

These compounds also exhibit a very good photochemical stability. Thus, under a laser radiation of 633 nm wavelength and 5 mwatt/m² power, a material comprising "Disper Red One" or DR1 (trade name of the Aldrich Company) dispersed in a PMMA matrix 14 μm in thickness exhibited a decrease in the extinction coefficient equal to 10% after only 1 min of exposure. In contrast, with the compounds of the invention, such a decrease was not observed even after 16 hours of exposure.

The compounds of the invention are employed in components of electrooptical or optical devices in the form of materials such as, for example, in the form of a film, by incorporation in a matrix such as a polymer, a resin and the like, according to conventional and known techniques.

Thus, for example, the molecules prepared according to Examples 1 to 6 were incorporated in a transparent polymer film from 0.5 to 200 μm in thickness, as described in European Patent No. 218,938. Polymethyl methacrylate (PMMA) and atactic polystyrene may be mentioned, for example, as suitable polymers. The polymer film was heated to a temperature above its glass transition temperature (Tg) and was then subjected to an intense electrical field to orient the active molecules in accordance with the invention. The film was then cooled to a temperature below the glass transistion temperature Tg, thus to freeze the oriented position of the active molecules.

A film containing oriented active molecules of the invention had an electrooptical coefficient r and a second harmonic generation coefficient which are comparable with those of the inorganic crystals usually employed in these applications, such as, for example, potassium diphthalate, ammonium diphthalate and potassium dihydrophthalate. In addition, the film exhibited specific advantages such as a low dielectric constant and an electrooptical activity of essentially electronic origin.

These materials, which are active in optoelectronics, especially in the form of a film, are capable of being employed in electrooptical modulators and active guides such as directional couplers, polarizers, integrated modulators and the like.

We claim:

1. A compound having the formula (I):

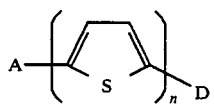 (I)

wherein:
A is an electron-acceptor group;
D is an electron-donor group; and
n is an integer from 1 to 10.

2. The compound of the formula (I) as claimed in claim 1, wherein:
D has the formula (II):

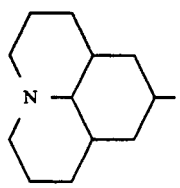 (II)

or is —$(R_2D_1)_m$ wherein $R_2$ is an aromatic hydrocarbon radical, m is an integer from 1 to 3, $D_1$ is a radical selected from the group consisting of amino, alkylamino, dialkylamino, arylamino, hydroxyl, thiol, alkylthio, arylthio, alkoxy, alkoxyphenyl, aryloxy, haloalkyl and oxy radicals; and wherein
A is a radical selected from the group consisting of nitro and cyano radicals, or is a compound of the formula (III):

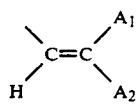 (III)

wherein $A_1$ and $A_2$ are not simultaneously hydrogen and are selected from the group consisting of hydrogen, cyano, nitro, phenyl sulfone and paranitrophenyl radicals, and —$PO_3(R_5)_2$ in which $R_5$ is a lower alkyl radical.

3. The compound of the formula (I) as claimed in claim 2, wherein $R_2$ is a phenylene radical.

4. The compound of the formula (I) as claimed in claim 2, wherein $R_5$ is an ethyl or propyl radical.

5. The compound of the formula (I) as claimed in claim 2, wherein $A_1$ and $A_2$ are selected from the group consisting of cyano and nitro radicals.

6. The compound as claimed in claim 5, wherein $A_1/A_2$ represent the cyano/cyano radicals.

7. The compound as claimed in claim 5, wherein $A_1/A_2$ represents the cyano/nitro radicals.

8. The compound as claimed in claim 5, wherein $A_1/A_2$ represent the nitro/cyano radicals.

9. The compound of the formula (I) as claimed in claim 2, wherein $D_1$ is a radical selected from the group consisting of

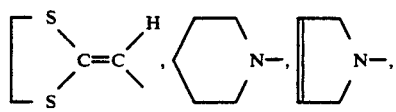

-continued

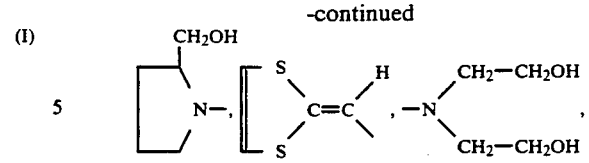

10. The compound as claimed in claim 1, wherein n is an integer from 1 to 4.

11. The compound of the formula (I) as claimed in claim 1 selected from the group consisting of:

(i)
(ii)
(iii)
(iv)
(v)

and (vi)

12. The compound of the formula (I) as claimed in claim 1, wherein D is selected from the group consisting of -continued

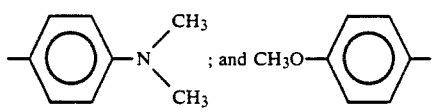

13. A material which is active in nonlinear optics and is capable of generating a harmonic of the second order, comprising at least one compound of the formula (I) as claimed in claim 1.

14. The material as claimed in claim 13, wherein the compound is incorporated into a matrix formed by a polymer matrix.

15. The material as claimed in claim 14, wherein the compound is incorporated into a polymeric film.

* * * * *

UNITED STATES PATENT AND TRADEMARK OFFICE
CERTIFICATE OF CORRECTION

PATENT NO. : 5,156,774

DATED : October 20, 1992

INVENTOR(S) : Frederic LEISING et al.

It is certified that error appears in the above-identified patent and that said Letters Patent is hereby corrected as shown below:

Abstract, line 1, "thiphene-related" should read --thiophene-related--.

Claim 2, column 11, line 24, "$-R_2D_1)_m$" should read -- $-R_2(D_1)_m$ --.

Claim 14, column 14, line 5, delete the word "matrix".

Signed and Sealed this

Twenty-eighth Day of September, 1993

Attest:

BRUCE LEHMAN

Attesting Officer

Commissioner of Patents and Trademarks